United States Patent
Blattner et al.

(10) Patent No.: US 11,031,094 B2
(45) Date of Patent: Jun. 8, 2021

(54) PROTEIN STRUCTURE PREDICTION SYSTEM

(71) Applicant: DNASTAR, INC., Madison, WI (US)

(72) Inventors: Frederick R. Blattner, Madison, WI (US); Steven J. Darnell, Madison, WI (US); Matthew R. Larson, Madison, WI (US); Amanda E. Mitchell, Madison, WI (US); John L. Schroeder, Madison, WI (US)

(73) Assignee: DNASTAR, INC., Madison, WI (US)

( * ) Notice: Subject to any disclaimer, the term of this patent is extended or adjusted under 35 U.S.C. 154(b) by 447 days.

(21) Appl. No.: 15/737,231

(22) PCT Filed: Jul. 15, 2016

(86) PCT No.: PCT/US2016/042581
§ 371 (c)(1),
(2) Date: Dec. 15, 2017

(87) PCT Pub. No.: WO2017/011779
PCT Pub. Date: Jan. 19, 2017

(65) Prior Publication Data
US 2018/0260517 A1    Sep. 13, 2018

Related U.S. Application Data

(60) Provisional application No. 62/193,225, filed on Jul. 16, 2015.

(51) Int. Cl.
| | | |
|---|---|---|
| *G16B 15/00* | (2019.01) | |
| *G16B 5/00* | (2019.01) | |
| *G16B 30/00* | (2019.01) | |
| *G16B 99/00* | (2019.01) | |
| *G06N 7/08* | (2006.01) | |

(52) U.S. Cl.
CPC .............. *G16B 15/00* (2019.02); *G06N 7/08* (2013.01); *G16B 5/00* (2019.02); *G16B 30/00* (2019.02); *G16B 99/00* (2019.02)

(58) Field of Classification Search
None
See application file for complete search history.

(56) References Cited

U.S. PATENT DOCUMENTS

| | | |
|---|---|---|
| 7,751,987 B1 | 7/2010 | Becker et al. |
| 2003/0130797 A1 | 7/2003 | Skolnick et al. |
| 2005/0267687 A1 | 12/2005 | Tomii |
| 2012/0271558 A1 | 10/2012 | Hur et al. |
| 2013/0304432 A1 | 11/2013 | Sander et al. |

FOREIGN PATENT DOCUMENTS

WO        2010-005925 A2    1/2010

OTHER PUBLICATIONS

International Search Report for PCT/US2016/042581 dated Nov. 29, 2016.
Written Opinion for PCT/US2016/042581 dated Nov. 29, 2016.

*Primary Examiner* — Michael L Borin
(74) *Attorney, Agent, or Firm* — Christopher M. Cabral; Much Shelist, PC

(57) ABSTRACT

The present invention is an accelerated conformational sampling method for predicting target peptide and protein structures comprising a process of determining energy minimized synthetic templates using a simple system for modeling individual molecular bonds within the subject peptide or protein. Use of these synthetic templates greatly reduces the computational resources necessary for optimally determining structural features of the target peptide or protein. The present invention also provides methods for rapid and efficient analysis of the effect of mutations on target peptides and proteins.

18 Claims, 16 Drawing Sheets

Specification includes a Sequence Listing.

Figure 4

```
For each template:

1. Calculate normal modes of motion
2. For each pair of modes (I,J):
   a. For each combination of weights (w,x):
   i.  Perturb template along I by w and along J by x
3. For each perturbation (n):
   a. Calculate the energy difference between the template
      and n
4. Synthetic template is conformation that has most negative
   energy difference along the trajectory.
5. Sort synthetic templates by score difference
6. For each synthetic template in 65$^{th}$ percentile:
   a. Replace original with synthetic template
```

Figure 8

```
Build Rapidly Expanding Random Tree with K vertices (Root
weights q_init, Vertices K, Interval Δq)
1. Setup initial Tree G based on (q_init)
2. While tree vertices < K and number of successive rejects <
   100:
   a. Set weights q_rand = Get Random Conformation of weights w_i
   b. Set weights q_near = Get Nearest Vertex(q_rand, G)
   c. For a incremental path between q_rand and q_near with interval
      (Δq)
    i. Set weights q_new = Create a New Conformation (q_prev + Δq)
   ii. Continue if chemical linkage test and collision test
       succeed; otherwise, set q_new = q_prev and break
   d. If q_new is not q_near, add a vertex (q_new) and add the edge
      (q_near, q_new) to Tree G; otherwise, reject vertex
3. Return Tree G Test Chemical Linkages
1. For each pair of atoms involved in a beta sheet hydrogen bond
   or disulfide
      a. Get the atom positions in the global frame
      b. Calculate the distance between the atoms
      c. If the distance exceeds tolerance then fail Sweep and Prune with Collision Test:
1. Project each segment S_i of the amino acid chain onto a
   directional vector to produce a 1D interval of extrema
   [minima m_i, maxima M_i] of each segment.
2. Sort the S_i by m_i and M_i to obtain a sorted list L of segment
   indices
3. Sweep L and update an active list A:
   a. Add segment Si to A when mi is retrieved from L and add
      all segments Si in A to a set of colliding pairs Pv
   b. Remove Si from A when maxima Mi is retrieved from L.
4. For each pair of colliding segments (S_i, S_j) in sets P_v, Test
   and Resolve Collisions. If resolved by changing rotamers,
   remove pair (S_i, S_j) from the P_v.
5. Return all sets of colliding segments P_v that were not
   resolved.

Test and Resolve Collisions: (Segments S_i, S_j)
1. Get the atom positions for S_i and S_j in the global frame
2. Perform a pairwise collision test for each atom atom_(i,m) in S_i
   against atom_(j,n) in S_j
3. If there is no collision then return Not Colliding.
4. If there is a collision
   a. For each available rotamer of (S_i and S_j), substitute a
      rotamer for either S_i or S_j
    i. If no collision with this pair of rotamers, then return
       Not Colliding
5. Return Colliding
```

PROTEIN STRUCTURE PREDICTION SYSTEM

CROSS REFERENCE TO RELATED APPLICATIONS

This application claims the priority of U.S. Provisional Patent Application No. 62/193,225 filed Jul. 16, 2015, the entire disclosure of which is incorporated herein by reference.

INCORPORATION OF SEQUENCE LISTING

A computer readable text file, entitled "070477-5002_US_ST25.txt" created on or about Apr. 9, 2019, with a file size of about 1 KB contains the sequence listing for this application and is hereby incorporated by reference in its entirety.

FIELD OF THE INVENTION

The invention generally relates to the fields of molecular biology, diagnostic science, and pharmacology, more particularly to identifying potential three-dimensional (3D) structures of protein molecules and to achieving therapeutic objectives by predicting drug or interactions with other proteins that may affect normal substrate binding or modulate the 3D structure of the protein in novel and useful modes.

BACKGROUND OF THE INVENTION

Throughout this application various publications are referred to in parentheses. Full citations to those references may be found at the end of the specification. The disclosures of these publications are hereby incorporated by reference in their entirety into the subject application to more fully describe the art to which the present invention pertains.

A guiding principle of structural biology is that a protein's amino acid sequence defines its tertiary (3D) structure, which is the shape of a protein molecule as defined by the geometric arrangement of its atoms [1]. Over the past half century, a revolution in biology and computer science has revealed the intimate relationship between a protein's biological function and its 3D structure and the feasibility of predicting a structure from sequence alone [2]. Accordingly, there is a pressing need for improved basic research and diagnostic tools and processes to improve protein engineering and drug development. These activities require high-resolution protein structures. Most protein structures are determined by X-ray crystallography: a slow, expensive, and unpredictable process. Much progress has been made in high-throughput structure determination [3], but a library of high-resolution structures for representative model organisms, including the human proteome, is beyond the reach of current experimental methods.

New protein sequences are discovered at a rate far exceeding that of protein structures. In 2014, the Universal Protein Resource (UniProt, the central repository of protein sequence data) was 407 times larger than the Protein Data Bank (PDB, the central repository of macromolecular structure data) with 4.3 million sequences versus 105,000 structures—and the gap continues to grow as it has for the past thirty years (FIG. 1). Considering that it can take months or years to solve a protein structure and the minimum cost per structure (for a structural genomics facility) is currently about $94,000 [4], protein structure prediction is the only way to close the sequence-structure gap. Current structure prediction techniques are classified as either ab initio or template-based.

Ab initio prediction methods [5-8] rely on an energetic force field (a mathematical model that estimates how biophysical forces affect thermodynamic stability) to fold protein sequences from basic principles. In current form, ab initio prediction is only applicable to short protein sequences (less than 150 residues) and require weeks of central processing unit (CPU) time. Most limiting is that current ab initio predictions are regarded as low-resolution models, which are insufficient for use in drug screening, drug design, ligand docking, or protein engineering by directed mutagenesis [9].

Template-based prediction methods, which use known experimental protein structures to guide the prediction process, are capable of producing "high resolution models" (indistinguishable from an experimental structure) and are used for industrial and pharmaceutical biosimulation needs. For example, these techniques have been successfully combined with small molecule docking processes to perform virtual screens that identified novel compounds for the inhibition of alpha-glucosidase (for treatment of diabetes) [10], Cdc25 and Shp2 phosphatase (for cancer treatment) [11, 12], and CK1 and ERK8 kinases (for the treatment of Alzheimer's disease and cancer) [13, 14]. Template-based methods can be further divided into homology modeling processes [15-18], which select templates based on sequence similarity to the query sequence, and protein threading processes [19-25], which select templates based on sequence-implied structural similarities with the query. The fundamental limitation of these methods is that they require a known experimental structure that is sufficiently similar to the target query.

The quality of a template-based prediction is reliant on how similar the conformations of the selected templates are to the native fold of the target protein. Templates are collected from protein structure databases and consist of entire or partial protein structures. The protein modeling community uses a variety of private and public structure databases combined with individualized sequence alignment, fold recognition, and domain search techniques to search for the best templates [26-32]. The query sequence is then mapped onto the selected templates to derive the final target protein model. Current approaches treat templates as static, rigid conformations; however, proteins are naturally flexible and plastic. As such, statistically significant templates may not adequately approximate the overall range of the target protein conformation, which leads template-based processes to converge toward suboptimal, non-native protein folds.

Hybrid approaches combine both ab initio and template-based prediction methods to improve predictive accuracy. One such example is the I-TASSER process [33-39], which is currently recognized as the best approach for predicting protein structures as determined by the Critical Assessment of Protein Structure Prediction (CASP) competition [40]. Since 2006, the I-TASSER process has won the biennial competition where teams worldwide blindly test their tools against unpublished protein structures. Fundamentally, hybrid approaches are still limited by their need of experimental structures for use as templates.

We present here an innovative protein structure prediction method—the NovaFold structure prediction process—that overcomes the critical barrier caused by incomplete template libraries. Rather than treating a template as rigid, it serves as a starting point for sampling the structural plasticity of the template fold. This accelerated conformational sampling increases structural diversity of the prediction process, which leads to the discovery of lower energy, more accurate structure predictions that are inaccessible to existing template-based techniques that rely solely on known structural templates. Examples presented here demonstrate how the invention can accelerate the design of improved biotherapeutics, such as antibodies. In addition, the NovaFold process can be used to advance the treatment of human disease by identifying the structural effect of genetic variation observed in patients suffering from harmful somatic mutations such as those found in cancer.

SUMMARY OF THE INVENTION

The present invention is directed to discovering the native 3D structure for a given protein by using synthetic templates to represent the range of putative structural conformations not captured in known experimental structures. A synthetic template can be derived from a template identified from conventional template-based prediction methods by perturbing it into alternate chemically-plausible conformations. The use of synthetic templates increases the sampled structural diversity of the prediction process well beyond that achieved by conventional ab initio and template-based techniques, with the effect of increasing the discovery rate of high resolution models with low energy conformations.

In one embodiment, a coarse grain mathematical model based on a mass-spring representation of a protein structure is used to calculate the resonant frequencies and associated modes of motion for a template, which are then used to extrapolate numerous candidate synthetic templates. This population is reduced to a single representative conformation using an energetic scoring function to produce one synthetic template. The process is applied to templates whose conformations are not already energetically optimal.

In yet another embodiment, the synthetic template process is applied to protein-protein complexes, where one or more proteins are bound to each other, such as antibodies comprised of heavy and light protein chains. Proteins in a complex exhibit a different mobility when compared to the individual proteins in isolation. As such, creating synthetic templates for a protein complex template ensures the process focuses on sampling chemically-plausible conformations that can be achieved by the complex as a whole.

In yet another embodiment, the synthetic template process is applied to predict conformational changes induced by site-directed mutations or genetic variations. Predictions are not limited to the immediate residues in contact with the mutation site. Affected residues can be several Angstroms away from the mutation or variant site. This analysis can accelerate protein engineering studies by predicting whether putative mutations will cause disruptive rearrangements to the protein's structure. The NovaFold process can improve human health by identifying structural mechanisms for how somatic mutations destabilize protein folds leading to destructive changes to cellular regulation such as those found in many cancers. These new mechanisms and high-resolution structure predictions will be invaluable to developing the next generation of structure-based drugs and biotherapeutics.

DESCRIPTION OF THE DRAWINGS

FIG. 4 summarizes the steps for creating synthetic templates for each template and for selecting synthetic templates for the modeling process. After the normal modes of motion are determined, each original template is perturbed along linear combinations of modes and each perturbation is evaluated by an energy scoring function. The templates are ranked based on their energetic difference from the original template and the synthetic templates are selected on the basis of having the most negative difference relative to the original template. To select the synthetic templates for inclusion in the prediction process, they are re-ranked by their score differences and the 65% with the most negative difference are selected to replace or supplement the corresponding original template.

FIG. 8 describes a preferred embodiment to create a synthetic template by using a rapidly expanding random tree structure, which organizes the search of an original template's conformational space. After calculating the set of normal modes (in terms of torsion angles) for an original template, the perturbations along individual modes are assigned weights ($w_i$) that correspond to amount of torsion angle change to apply to the model along a given mode. Expanding a random tree explores a high-dimensional combination of normal mode weights, and thus conformational space. In this process, atomic collisions within the model are detected and an effort is made to resolve collisions involving side chain atoms. After exhaustively searching the conformational space defined by the normal modes, the lowest energy model is selected to represent the synthetic template.

DETAILED DESCRIPTION OF THE INVENTION

Figure 1:
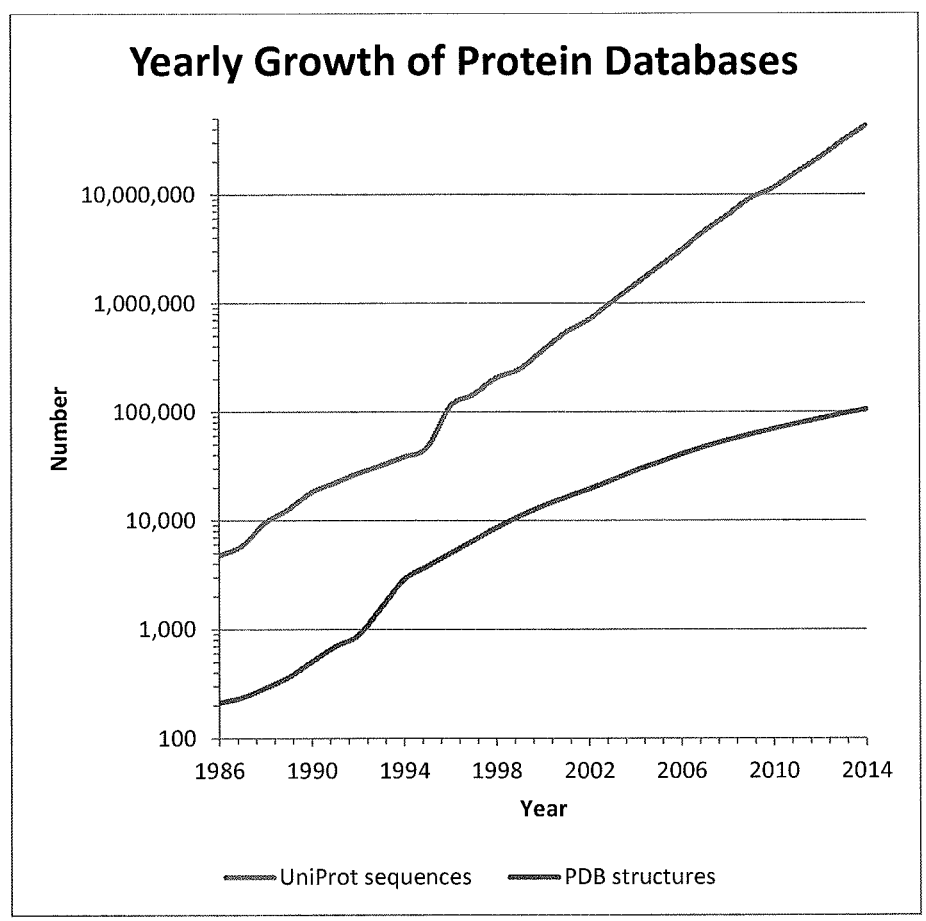
FIG. 1 represents the yearly growth of the UniProt and PDB protein databases, illustrating the divergence between known protein sequences and known protein structures, respectively. The decrease in rate of known protein structures and the continued logarithmic accumulation of protein sequences indicates the increasing dearth of relevant templates for template-based structure prediction methods.
Figure 2:
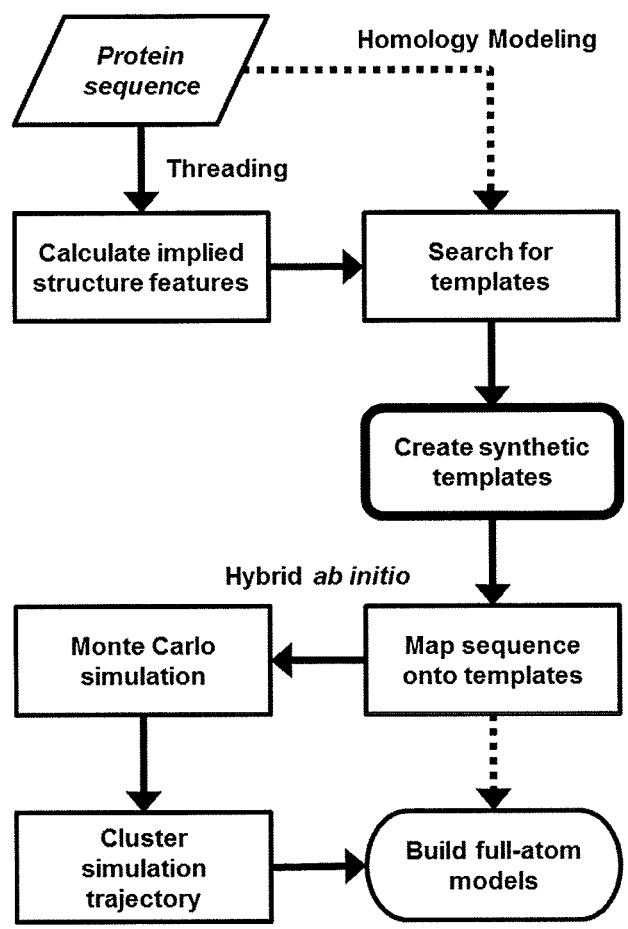
FIG. 2 depicts the use of the present invention (bold and shaded) within three different template-based structure prediction methods: homology modeling, protein threading, and the hybrid ab initio approach used by the NovaFold structure prediction process. All three methods begin by selecting suitable conventional templates by methods known to those skilled in the art [26-32]. The invention disclosed here then constructs synthetic templates to represent the greater structural diversity of permissible structural variants of the selected conventional templates for the remaining steps of the modeling process. In the NovaFold approach, an additional two-step simulation procedure is used to perturb the templates into more energetically favorable conformations. Finally, in all three methods, the remaining backbone and side chain atoms are added to the structure and energetically minimized to produce the final structure predictions. The NovaFold process, which is the most accurate and preferred approach, is highlighted by solid black arrows. The alternate and less accurate approaches are marked by dotted lines.

The present invention comprises an accelerated conformational sampling process to construct high-resolution models for a target protein sequence, where synthetic templates are used to construct new, low energy conformations that were otherwise undiscoverable by conventional structure prediction techniques. The use of synthetic templates within otherwise conventional template-based structure prediction methods is summarized in FIG. 2. The accelerated conformational sampling process comprises creating synthetic templates using normal mode analysis (NMA), a structural mass-spring model that describes protein motion at resonant frequencies, to build biologically relevant conformations from a given structure template. The process can generate a synthetic template within minutes; as such, it is applied to dozens of templates associated with a structure prediction. A structure prediction is said to undergo accelerated conformational sampling when synthetic templates are used in the prediction's downstream conformational search and refinement steps. For example, FIG. 3 outlines the use of accelerated conformational sampling in the context of the I-TASSER hybrid ab initio structure prediction approach.

Figure 3:
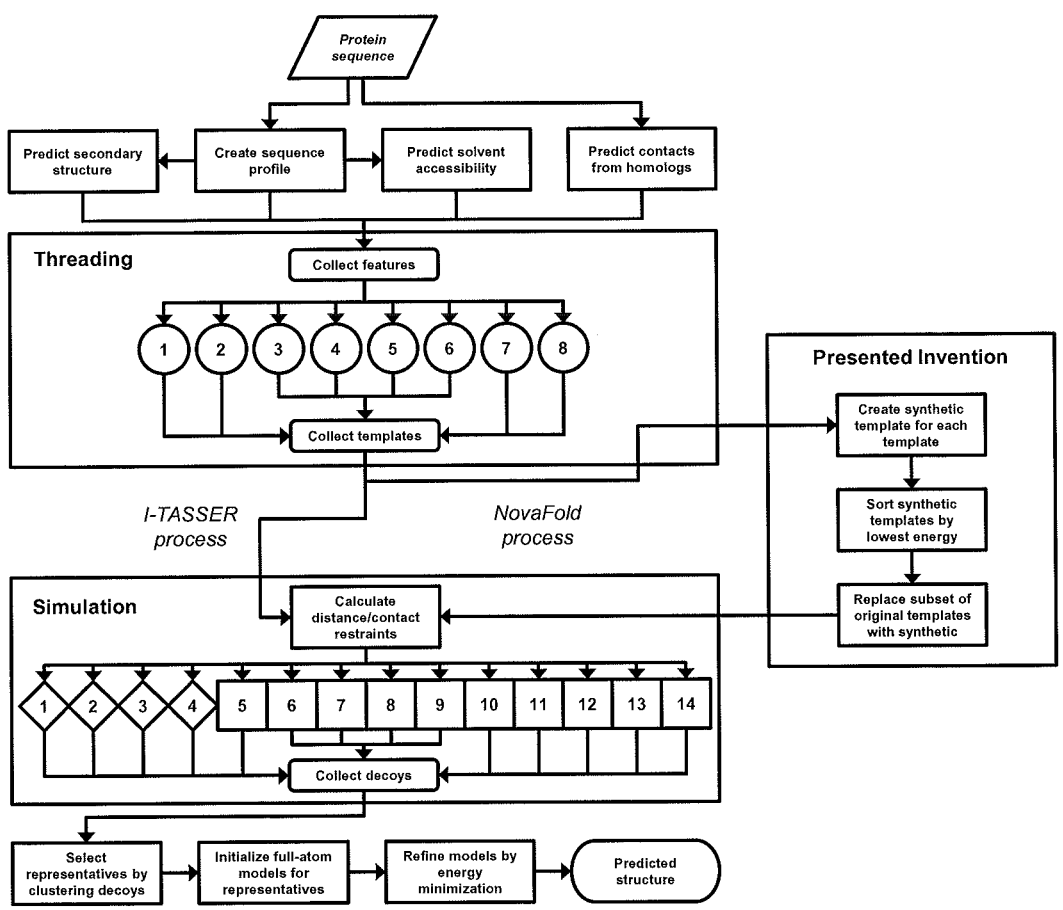
FIG. 3 depicts the synthetic template and accelerated conformational sampling process used in the NovaFold structure prediction process as described in Detailed Description of the Invention.

The structure prediction process outlined in FIG. 3 begins by performing two sequence-based searches for each query protein sequence. The first search, a PSI-BLAST sequence similarity search [42] against a non-redundant database of known protein sequences (sequences to display: 1000, passes: 3, e-value threshold: 0.001), identifies similar sequences and constructs a sequence profile matrix of amino acid frequencies observed along the sequence. The sequence profile matrix is used by two separate machine learning models that predict the secondary structure classifications and the relative solvent accessibility for each residue. The second search is a local pairwise sequence alignment against a non-redundant structural feature database, where the identified homologous proteins are used to predict internal contacts for each residue. The information from both searches, as well as any additional structural classification or solvent accessibility information, is consolidated into a collected feature matrix. Next, one or more different protein threading models align the query's collective features against the non-redundant structure database to select statistically significant original templates. The number of different protein threading models necessary to generate a significant number of original templates may be between one and forty, preferably between six and twelve and most preferably eight. Nearly 100 original templates are typically collected.

At this point, the NovaFold process implements the accelerated conformational sampling process, whose details are schematically presented in FIG. 4. Normal mode analysis (NMA), which is based on a harmonic approximation to describe the fluctuation of a potential energy function around a structure template [43, 44], is used to calculate the normal modes of motion for each template selected from the threading process. First a potential energy is established where contacting residues are identified using a cutoff distance. The potential (v) is defined as $$V_{ij} = \sum_{s_{ij}^o < R_c} \frac{\gamma}{2}(s_{ij} - s_{ij}^o)^2$$

where $s_{ij}$ is the distance between atoms i and j, $s_{ij}^o$ is the distance between the atoms in the original structure, $\gamma$ is the spring constant, and $R_c$ is the cutoff distance (typically about 7 Å). Next a Hessian matrix, the second derivatives of the potential energy matrix, is calculated. The second derivatives of the potential evaluated at the equilibrium position for off-diagonal elements are $$\frac{\delta^2 V_{ij}}{\delta x_i^2} = \frac{\gamma}{s_{ij}^2}(x_j - x_i)^2$$

$$\frac{\delta^2 V_{ij}}{\delta x_i \delta y_j} = \frac{-\gamma}{s_{ij}^2}(x_j - x_i)(y_j - y_i)$$

where similar expressions hold for the y and z-components. For on-diagonal elements, the second derivatives are $$\frac{\delta^2 V_{ij}}{\delta x_i^2} = \gamma \sum_j \frac{(x_j - x_i)^2}{s_{ij}^2}$$

$$\frac{\delta^2 V_{ij}}{\delta x_i \delta y_j} = \gamma \sum_j \frac{(x_j - x_i)(y_j - y_i)}{s_{ij}^2}$$

The Hessian matrix ($\mathcal{H}$) describes the forces along the x, y, and z-components for each of n residues in the protein $$\mathcal{H} = \begin{bmatrix} H_{11} & \cdots & H_{1n} \\ \vdots & \ddots & \vdots \\ H_{n1} & \cdots & H_{nn} \end{bmatrix}$$

$$\mathcal{H}_{ij} = \begin{bmatrix} \partial^2 V/\delta x_i \delta x_j & \partial^2 V/\delta x_i \delta y_j & \partial^2 V/\delta x_i \delta z_j \\ \partial^2 V/\delta y_i \delta x_j & \partial^2 V/\delta y_i \delta y_j & \partial^2 V/\delta y_i \delta z_j \\ \partial^2 V/\delta z_i \delta x_j & \partial^2 V/\delta z_i \delta y_j & \partial^2 V/\delta z_i \delta z_j \end{bmatrix}$$

Finally, LU (lower-upper) decomposition of the Hessian matrix produces the normal modes of motion (eigenvectors) and their associated frequencies (eigenvalues). The Hessian matrix is represented as a sparse matrix and decomposed into modes and frequencies using ARPACK (Department of Computational and Applied Mathematics, Rice University, Houston, Tex.) and the Intel Math Kernel Library (Intel Corp., Santa Clara, Calif.). The six lowest frequency modes representing trivial translational and rotational degrees of freedom are ignored. The remaining normal modes describe collective motions throughout the protein structure, where each residue is assigned an independent vector describing its velocity through Cartesian space.

Next, new conformations are constructed by perturbing the template along linear combinations of the ten lowest frequency normal modes. A discrete set of weights (ranging from −80 to 80, incremented by values of 20) are selected to limit the number of new conformations to approximately 3000 per template—amounting to over 300,000 perturbed conformations for each structure prediction. Each conformation is evaluated with an energetic scoring function [45], whose most important factors are short-range residue contacts, hydrogen bonding, and secondary structure propensities, and then compared against the score for the original template. The synthetic template is identified as the conformation with the most negative difference in energy score compared to the original template. Synthetic templates that improve the accuracy of the prediction are associated with large, negative differences in score compared to their respective original templates. To identify these useful synthetic templates, the entire set is sorted based on their score difference and those in the 65$^{th}$ percentile are selected to replace their original template counterparts.

Processes that use a reduced protein representation, such as that in use by NMA in the accelerated conformational sampling technique, do not sacrifice overall model accuracy since an all-atom model refinement remains part of the prediction process. In fact, NMA is more adept than all-atom approaches like molecular dynamics (MD) at modeling biological motions occurring at the micro- to millisecond time scale [43, 44]. NMA can generate these conformations in minutes of process time while MD requires weeks or months of process time, which greatly improves the practicality of the applying the accelerated conformational sampling process on a large scale.

Figure 5:
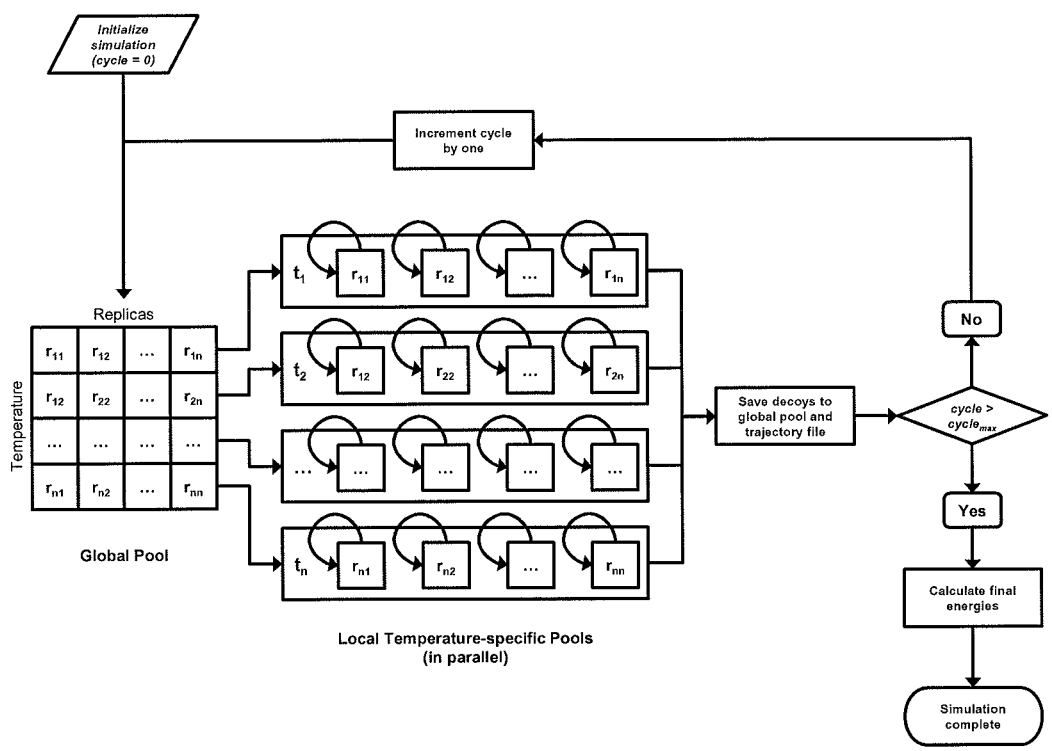
FIG. 5 depicts how decoy structures are created by the NovaFold simulation process. A simulation is started by initializing the decoy pool with the query protein mapped onto the selected templates, synthetic or otherwise. The simulation occurs over a series of temperatures, which are processed in parallel. For each temperature, a local pool is constructed. For each decoy in the local pool, a series of random perturbations (or "moves") are performed and evaluated by the energy function. Moves are accepted based on the Metropolis criterion. For each cycle, the global pool is synchronized and the updated decoys are saved. The simulation continues for a defined number of cycles or until a time limit elapses.

Selected templates are then used to start fourteen Monte Carlo Markov Chain (MCMC) simulations [45] in order to search the for low energy conformations of the query protein. Physical pairwise distance restraints and internal residue contacts are calculated from the templates and then mapped onto the query protein using the threading alignment. Four simulations use free ab initio modeling techniques (diamonds in FIG. 3), where any randomly selected peptide bonds can be perturbed. The remaining ten simulations use template-based techniques (squares), where regions associated with a template cannot be perturbed. The common process between these two simulations types are presented in FIG. 5. Each simulation has a "decoy pool," a set of chemically plausible conformations that is updated with lower energy conformations over the course of the simulation. The global pool is a square matrix where a list of decoys is maintained over a range of simulation temperatures. The decoy list length is dependent on protein chain length: 40 decoys for proteins less than 165 residues, 50 decoys for proteins between 165 and 240 residues, 60 decoys between 240 and 300, 70 decoys between 300 and 400, and 80 decoys for proteins greater than 400 residues.

The simulations proceed for a predetermined number of simulation cycles (ab initio: 250, template-based: 500) or 50 CPU hours. For each temperature, a local decoy pool is constructed and each individual decoy is randomly perturbed for as many residues that are allowed to move in that decoy. Local data structures are used such that this step can be performed in parallel.

Perturbations are limited to five basic movements: 1) moving two or three consecutive bonds, 2) moving two consecutive instances of the first type, 3) translating six to twelve consecutive bonds as a rigid group, 4) inducing a sequence-shift by permuting a three bonds fragment with a two bond fragment, 5) and constructing a random conformation between two distant residues. The old and new decoys are evaluated by a knowledge-based potential energy function that considers correlations between contacting residue types, local structural stiffness caused by hydrogen bonding, template-derived distance and contact restraints, long range pairwise interactions, electrostatic interactions, and contact order (average sequence separation between contacting residues). Random moves are accepted and rejected based on the Metropolis criterion as follows. The potential energy of the change ΔU is calculated for the move and if ΔU<0 the movement is automatically accepted. If instead AΔU>0, then calculate a probability cutoff to accept the move as $P_{acc}=e^{-\Delta U/T}$ where T is a temperature value at the stage in the simulation. A random number r is generated between 0 and 1. If $P_{acc}$>r, then the move is accepted. If accepted, the new decoy replaces the old. If rejected and the simulation is template-based, a single recovery step is attempted where the fragment is repositioned by rotation and translation. Afterwards, the global pool is synchronized with the updated local pools and the decoys are saved in a trajectory file. In total, tens of thousands of chemically-plausible conformations are recorded across all simulations.

Next, all of the decoy trajectories are collected and clustered by the k-means method into ten clusters. The center-most representative of each cluster is selected for final refinement, in which backbone and side chain atoms are added to the selected scaffold and a MCMC energy minimization repacks the side chains and relaxes the backbone atoms into the final low energy conformation, resulting in the final predicted structures.

The Examples describe several instances wherein the accelerated conformational sampling approach produces more accurate predicted structures that are highly similar to the known experimental structure. For these examples, all conditions are held constant except for the use of synthetic templates. If we assume that given enough time the MCMC simulation can always produce a prediction equivalent to the accelerated method, these examples clearly illustrate that accelerated conformational sampling increases the speed of discovering these solutions. Given the stochastic nature of the MCMC process, one cannot estimate how much additional computation effort is required—it may be weeks, months, or longer. Simulation methods are also prone to blockage by thermodynamic and kinetic barriers in the folding energy landscape and may never discover a distant native conformation. The present invention is not restricted by these barriers, which increases the structural diversity of the approach and the frequency of discovering near-native conformations. As a result, the use of synthetic templates accelerates the creation of high-resolution models and improves the rate of success for both easy and difficult modeling problems.

A person skilled in the art would understand that synthetic templates address a critical need to represent unobserved structural plasticity in order to improve the accuracy of template-based structure prediction processes. The construction of high-resolution models is hindered by selecting templates whose conformations are structurally distant to the biologically relevant conformation of the target, regardless if the template represents the correct topological fold. Given the limited number of known structures in the PDB, this situation is expected to occur often. In addition, a skilled person would recognize that selecting a single, useful synthetic template from a population of thousands of unnatural perturbations is not obvious. One could use MD [46, 47], Monte Carlo (MC) perturbation [48], and all forms of NMA to perturb a template; however, the blind inclusion of suboptimal synthetic templates will decrease the quality of the resulting prediction. One could also use an alternative scoring function to select a putative synthetic template; however, this approach is still reliant on the key insights introduced by the invented process. As evidenced by the absence of the invented process in the leading structure prediction methods and by the application of the process to create higher resolution models (see Examples), the synthetic template approach is unique, practical to use, and solves the problem of constructing better structure prediction templates without additional target-specific experimental data.

A. Definitions

As used herein, the term "3D structure" refers to the three-dimensional shape of a protein molecule as defined by the geometric arrangement its atoms, which is also commonly referred as the molecule's "tertiary structure."

As used herein, the term "root mean squared deviation" or "RMSD" refers to the average distance measured in Angstroms (Å) between atoms in superimposed protein structures, where a lower value indicates a better structural match.

As used herein, the term "high resolution model" refers to a predicted 3D structure indistinguishable from a known experimental structure of that protein, which is defined as an RMSD less than 2 Å.

As used herein, the term "conformational space" refers to the set of all chemically-plausible structural arrangements for a protein.

As used herein, the term "synthetic template" refers to an unnatural structure template that represents an alternate chemically-plausible conformation for a protein that has not been observed in known experimental structures.

As used herein, the term "accelerated conformational sampling" refers to the process of using synthetic templates to overcome energetic and kinetic barriers to discover native, low energy conformations that were otherwise undiscoverable by conventional structure prediction techniques.

B. Techniques for Using Synthetic Templates

The methods and compositions described herein detail how synthetic templates produced by the present invention can be used in a structure prediction process.

For template-based structure prediction methods that rely on a single template, the target protein sequence is simply mapped onto the synthetic template scaffold rather than the original template if the synthetic template has a lower energetic score than the original. This is a direct one-to-one replacement.

Different techniques are required for template-based structure prediction methods that rely on multiple templates.

Figure 6:
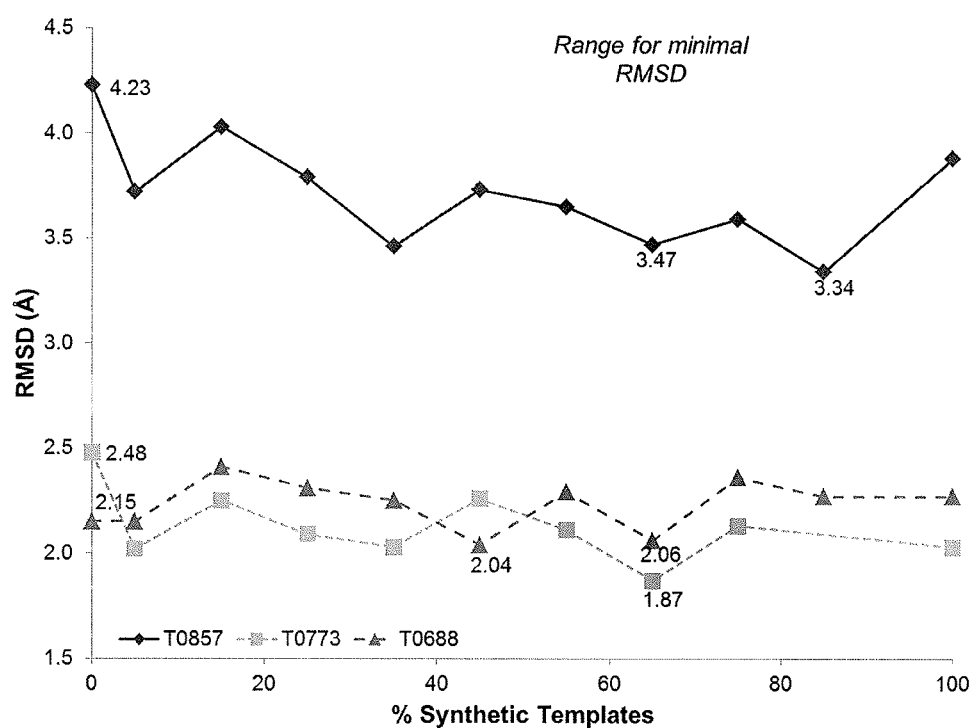
FIG. 6 depicts the optimal range for the number of synthetic template substitutions that minimize the RMSD of the resulting predicted structure to the known experimental structure. For each of the examples, the optimal substitution range for the identified 80 original templates is nearly between the $50^{th}$ and $80^{th}$ percentiles. For CASP ID T0857 and T0688, the minimal RMSD model lies just outside this range, but near-minimal models for each are predicted when using a synthetic template ratio of 65%.

For n templates, there are up to n individual synthetic template substitutions possible. Non-intuitively, replacing all top ranked threading templates with synthetic templates results in a decreased prediction accuracy (the structural similarity as measured by RMSD between the predicted structure and the known experimental structures is worse than that for the unmodified approach). The technique is successful when substitution is focused only on a subset of the synthetic templates. As discussed in FIG. 4, all putative synthetic templates are evaluated by an energetic scoring function that approximates the biophysical forces that mediate protein folding, which is calculated by performing one round of MCMC simulation [35, 45]. The synthetic templates are re-ranked using the energetic score difference between each synthetic template and its original template. We consistently observe improved end-result RMSD values when 65% of the original templates are replaced with synthetic templates having the most negative energetic score differences. FIG. 6 indicates that a synthetic template substitution ration between 50% and 80% is appropriate for structure predictions with an initial set of 80 templates. The number of synthetic template substitutions changes proportionally as the number of initial templates changes. Finally, we vary the proportion of synthetic-to-original templates between independent MCMC simulations (55%, 65%, 75%, and 85%) to reduce the likelihood that the simulations oversample conformations from the same local energy minima.

EMBODIMENTS

The following are among the embodiments of the invention.

A method for creating NMA-based perturbations for synthetic template construction is to perturb a protein structure along the principal vector defining a normal mode or along discrete linear combinations of modes. The method is straightforward to apply; however, its use does not scale well beyond pairwise combinations of normal modes. Also, since normal modes are conventionally linear vectors, implausible bond stretching and bending will occur as the deformation magnitude increases. Energetic minimization processes, like those present in hybrid ab initio structure prediction, are used to correct chemically-implausible deformations.

Biomacromolecular structures can be represented by either Cartesian coordinates or by an internal coordinate system describing bonds and bond angles within the atomic structure. A preferred method for creating NMA-based perturbations is to map normal modes from linear Cartesian vectors to changes in torsional angles, which describe the rotations of the protein backbone around the bonds containing each residue's carbon-alpha (Cα) atom, and perturb the structure strictly along torsion angles. This "rigid geometry" approach conserves bond lengths and angles and always generates a chemically-plausible conformation. High-strain torsion angles are still possible, but they remain more energetically favorable than impossibly long bonds or contorted angles.

Figure 7:
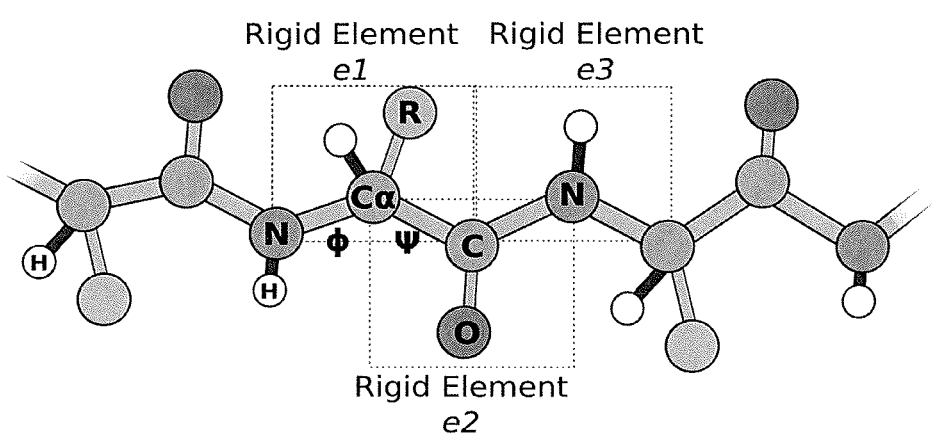
FIG. 7 depicts the relative coordinate system representing a structure's internal coordinate system. A rotational transformation is defined by the torsion angle around the vector defined from the local origin atom to a neighboring origin atom and the translational transformation is defined by the vector itself. As shown, the vector for rigid element e1 is defined from the $C_\alpha$ atom position to the C atom position and has a rotational degree of freedom around the $\Psi$ angle. The full transformation for rigid element e2 is expressed as a matrix representing the torsion angle rotation across the $C_\alpha$—C bond and the positional translation along the length of the bond.
Figure 9:
FIG. 9 depicts improvements achieved by the invention in predicting the structure of the BT2437 protein. The two beta strands in the forefront are highlighted for the known structure (dark gray) and the improved model (light gray). The same regions for the original model (black) are designated as loops.

An embodiment of an internal coordinate system involves dividing a structure into rigid elements whose motion is restricted to rotations about the bonds of the protein chain. A rigid element is a minimal unit of a protein over which its associated atoms remain fixed during perturbation. In FIG. 7, a rigid element (e1) and a subsequent element (e2) are highlighted. Each rigid element contains one or more atoms and its local frame of reference is centered on a key atom (e.g. Cα for element e1, C for element e2). The 3D conformation of a protein structure is defined by a series of rigid elements, each with an independent rotation and translation relative to its preceding element. Amino acid side chains are represented as a rotamer, a conformational isomer whose atomic positions are defined by torsion angles, that is defined using the original structure or selected from a library of rotamers. Carbonyl and nitrogen groups are represented by separate rigid elements even though the connecting peptide bond constraints the atoms into a fixed planar group. In addition, the restricted geometry of proline residues and the steric interactions between neighboring atoms will further constrain rotatable bonds.

The position and orientation of a local frame is described relative to its prior element along the protein backbone by a 4×4 rotational and translational matrix. Similarly, the subsequent local frame is described relative to the current frame by a 4×4 rotational and translation matrix. Multiplication of these matrices is used to derive the orientation of any given reference frame in the chain. If atom 1 is placed at a reference frame origin and the subsequent reference frame origin for atom 2 is referenced by vector $V=[t_x, t_y, t_z]$ defined along the bond between atoms 1 and 2, then the rotation around V (such as a torsion angle) is described by a rotation matrix R and a translation matrix T. The R and T matrices are combined as a single rotation-translation matrix (RT).

$$RT = \begin{bmatrix} r_{11} & r_{12} & r_{13} & t_x \\ r_{21} & r_{22} & r_{23} & t_y \\ r_{31} & r_{32} & r_{33} & t_z \\ 0 & 0 & 0 & 1 \end{bmatrix}$$

RT describes a right-handed coordinate system whose axes satisfy the right-hand rule. Obtaining global Cartesian coordinates for an atom with position $V=[x_i, y_i, z_i, 1]$ in a local frame then involves the chained matrix multiplications of all the prior RT matrices:

$$(x_g, y_g, z_g, 1) = RT_1 \times RT_2 \ldots \times RT_i(x_i, y_i, z_i, 1)$$

NMA-based perturbations distort a protein structure along the vector defining a principal normal mode or a discrete linear combination of modes. To satisfy the rigid geometry approximation, normal modes must be converted from displacements in Cartesian space to changes in internal dihedral angles. The Cartesian displacement coordinates are related to the internal rotations as defined by the Wilson s-vector method [49]:

$$s = Bd$$

where s is a vector of internal coordinates, d is a vector of Cartesian displacement coordinates, and B is a matrix of constants determined by the geometry of the molecule. The normal modes are mapped to a quaternion [tx, ty, tz, θ] that describes a vector representing the bond between two atoms with torsion angle θ. The rotation matrix determined from this quaternion is used to update the original rotation matrix R and to construct a new RT matrix that includes the normal mode distortion.

An embodiment for exploring the chemically-plausible conformational space along an arbitrary number of normal modes is to use a rapidly exploring random tree (RRT) [50] data structure combined with a collision detection process (FIG. 8). An RRT encourages incremental perturbations towards unexplored portions of an original template's conformational space and efficiently supports the search along a combination of dozens of normal modes, rather than simple pairwise combinations. In addition to using a rigid geometry approximation, a chemical restraint process and a collision detection process screen for movements that cannot physically occur, which stops further searching along that particular combination of normal modes. The approach replaces the use of a time-consuming energetic calculation with a fast validation of atomic geometry. These two processes are summarized in FIG. 8 and described in detail below.

The RRT structure defines a conformation as a vector of weights $w_i$ of size equivalent to the number of normal modes used for the exploration (effectively an arbitrary number, but typically 20 modes for modeling large concerted motions and 50 modes for modeling local fluctuations). The sampling of conformational space increases as the tree structure grows, which involves creating a random conformation by generating a new set of weights, incrementally perturbing the nearest saved conformation toward the new conformation, and adding new plausible conformations to the tree. Each incremental change is evaluated for preserving chemical linkages (hydrogen bonds between strands in a beta sheet and disulfide bonds) and preventing atomic clashes (described later). The linkage geometry is determined from the unperturbed structure. To determine whether a linkage restraint is conserved, the Cartesian coordinates for atoms involved in linkages are calculated and the distance between pairwise atoms involved in the linkages are evaluated. For collisions involving side chain atoms, alternate rotamers are screened for poses that resolve the clash. If the collision cannot be resolved, the last valid conformation is added as a leaf node to the previous saved conformation and the cycle repeats itself. RRT expansion ends when the tree reaches a maximum size, a series of sequential attempts to expand the tree fail (typically 100 attempts), or a time limit is exceeded (typically ten minutes).

Collision detection is implemented as a one-dimensional Sweep and Prune (SAP) process [51, 52]. SAP is a sorting-based technique that examines the overlap between bounding boxes around rigid elements. The process is optimal for collections where all elements move incrementally, such as the concerted motions described by normal modes. For a given conformation, the extrema of the bounding boxes are projected onto a vector defined by the original template's N-terminal nitrogen and C-terminal carbon, and then a linked list of the elements is sorted by their projected minima. Potential overlapping pairs of elements are identified based on whether their minima overlap, then all atom pairs between the two elements are tested for collisions by identifying overlapping hard spheres with van der Waals radii (typically 80% of ideal values to account for allowable soft penetration). Subsequent collision detection for incremental movements requires less time because the elements are now partially sorted. This embodiment is the first SAP process to consider an all-atom representation of a protein with residue-specific side chains, which is a critical requirement for accurately detecting atomic clashes within a protein structure.

The RRT process is used to sample the accessible conformational space for an original template along a set of many normal modes, which creates a set of putative synthetic templates with greater structural diversity than those achievable using simple pairwise combinations of normal modes. Finally, the established process for selecting a synthetic template is applied to this resulting set. This process is repeated for every template selected by protein threading and the associated synthetic templates are integrated into the prediction process as previously described. At this point, the NovaFold process, which includes the present invention and the I-TASSER process, converges with the I-TASSER process (FIG. 3). As demonstrated in the Examples, the NovaFold process provides a clear advantage over other methods by improving the accuracy of structure prediction over a wide range of medically-relevant targets, including antibody complexes and integral membrane proteins.

In a particular embodiment of the invention, a conformational sampling method for predicting the structure of an amino acid sequence is applied to an amino acid sequence. The conformational sampling method comprises:

a) creating a sequence profile matrix of the amino acid sequence;

b) determining an alignment of each respective residue of the amino acid sequence against the sequence profile matrix;

c) identifying internal contacts for one or more residues in the plurality of residues using the alignment;

d) collecting the features of the sequence profile matrix and internal contacts for each residue in the plurality of residues into a collected feature matrix;

e) aligning the collected feature matrix using one or more threading models with a structural feature database of original templates;

f) selecting a plurality of optimally aligned original templates from the aligning e);

g) calculating normal modes of motion for each original template in the plurality of optimally aligned original templates;

h) perturbing each respective original template in the plurality of optimally aligned original templates, for each pair of calculated normal modes, thereby collectively creating a plurality of synthetic templates;

i) scoring the energy difference between each original template and the corresponding synthetic template;

j) selecting a subset of synthetic templates from the plurality of synthetic templates based on satisfaction of a predetermined cut-off criterion;

k) replacing or supplementing the original templates in the plurality of optimally aligned original templates with the corresponding selected subset of synthetic templates to generate a plurality of modeling templates;

l) calculating distance and contact restraints within modeling templates of the plurality of modeling templates;

m) performing, with modeling templates in the plurality of modeling templates, Markov Chain Monte Carlo simulations, thereby obtaining simulation results;

n) clustering the simulation results, wherein the clustering comprises a plurality of clusters, each cluster in the plurality of clusters representing models from the performing m);

o) selecting representative models of each cluster in the plurality of clusters;

p) refining the representative models of the selecting o) by energy minimization; and q) selecting the lowest energy refined representative model as the predicted structure of the amino acid sequence.

In another embodiment of the invention, a computer system is programmed to predict the structure of an amino acid sequence, the computer system comprising at least one processor and memory storing at least one program for execution by the at least one processor, the at least one program comprising instructions for:

a) creating a sequence profile matrix of the amino acid sequence;

b) determining an alignment of each respective residue of the amino acid sequence against the sequence profile matrix;

c) identifying internal contacts for one or more residues in the plurality of residues using the alignment;

d) collecting the features of the sequence profile matrix and internal contacts for each residue in the plurality of residues into a collected feature matrix;

e) aligning the collected feature matrix using one or more threading models with a structural feature database of original templates;

f) selecting a plurality of optimally aligned original templates from the aligning e);

g) calculating normal modes of motion for each original template in the plurality of optimally aligned original templates;

h) perturbing each respective original template in the plurality of optimally aligned original templates, for each pair of calculated normal modes, thereby collectively creating a plurality of synthetic templates;

i) scoring the energy difference between each original template and the corresponding synthetic template;

j) selecting a subset of synthetic templates from the plurality of synthetic templates based on satisfaction of a predetermined cut-off criterion;

k) replacing or supplementing the original templates in the plurality of optimally aligned original templates with the corresponding selected subset of synthetic templates to generate a plurality of modeling templates;

l) calculating distance and contact restraints within modeling templates of the plurality of modeling templates;

m) performing, with modeling templates in the plurality of modeling templates, Markov Chain Monte Carlo simulations, thereby obtaining simulation results;

n) clustering the simulation results, wherein the clustering comprises a plurality of clusters, each cluster in the plurality of clusters representing models from the performing m);

o) selecting representative models of each cluster in the plurality of clusters;

p) refining the representative models of the selecting o) by energy minimization; and q) selecting the lowest energy refined representative model as the predicted structure of the amino acid sequence.

In a further embodiment of the invention, includes a non-transitory computer readable storage medium storing a computational module for predicting the structure of an amino acid sequence, wherein the computational module comprising instructions for:

a) creating a sequence profile matrix of the amino acid sequence;

b) determining an alignment of each respective residue of the amino acid sequence against the sequence profile matrix;

c) identifying internal contacts for one or more residues in the plurality of residues using the alignment;

d) collecting the features of the sequence profile matrix and internal contacts for each residue in the plurality of residues into a collected feature matrix;

e) aligning the collected feature matrix using one or more threading models with a structural feature database of original templates;

f) selecting a plurality of optimally aligned original templates from the aligning e);

g) calculating normal modes of motion for each original template in the plurality of optimally aligned original templates;

h) perturbing each respective original template in the plurality of optimally aligned original templates, for each pair of calculated normal modes, thereby collectively creating a plurality of synthetic templates;

i) scoring the energy difference between each original template and the corresponding synthetic template;

j) selecting a subset of synthetic templates from the plurality of synthetic templates based on satisfaction of a predetermined cut-off criterion;

k) replacing or supplementing the original templates in the plurality of optimally aligned original templates with the corresponding selected subset of synthetic templates to generate a plurality of modeling templates;

l) calculating distance and contact restraints within modeling templates of the plurality of modeling templates;

m) performing, with modeling templates in the plurality of modeling templates, Markov Chain Monte Carlo simulations, thereby obtaining simulation results;

n) clustering the simulation results, wherein the clustering comprises a plurality of clusters, each cluster in the plurality of clusters representing models from the performing m);

o) selecting representative models of each cluster in the plurality of clusters;

p) refining the representative models of the selecting o) by energy minimization; and q) selecting the lowest energy refined representative model as the predicted structure of the amino acid sequence.

EXAMPLES

The following examples demonstrate how the use of synthetic templates and the accelerated conformational sampling method of the present invention produce higher resolution, more accurate models than those created by an unmodified hybrid ab initio process ("original process"). The examples are offered to illustrate this invention and are not to be construed as limiting the scope of the present invention. These examples were selected from the targets for the CASP10 (Critical Assessment of Structure Prediction) competition, where teams worldwide test their tools against unpublished protein structures [40]. A blind test was performed such that the template library used by each method was frozen at a period in time before the examples' experimentally determined structures were published in the PDB. For each example, the predicted models from each method were structurally aligned to the experimentally determined structure and the RMSD between each pair was calculated. Table 1 summarizes the improvements for all examples using the presented invention.

TABLE 1

Summary of accuracy improvements achieved by the accelerated conformational sampling method for seven example proteins.

| Example | Original vs Known (RMSD) | Invention vs Known (RMSD) | Percent improvement |
| --- | --- | --- | --- |
| 1 | 2.21 | 1.64 | 26% |
| 2 | 2.04 | 1.25 | 39% |
| 3 | 2.27 | 1.81 | 20% |
| 4 | 2.15 | 1.84 | 14% |
| 5 | 2.19 | 1.78 | 19% |
| 6 | 2.21 | 1.75 | 21% |
| 7 | 1.74 | 0.96 | 45% |

RMSD between the predicted structure from the original method and the presented invention is calculated against the experimentally determined structure and the percent improvement of the structure predicted by the invention is listed.

The examples below detail the particular structural elements that were improved by the presented invention, which led to the observed improvements in RMSD.

Example 1

Improved Secondary Structure Prediction of BT2437

The protein BT2437 from *Bacteroides thetaiotaomicron* VPI-5482 contains the domain DUF4136 at the core of the protein [53] (PDB ID: 4F54). The accelerated conformational sampling process correctly identified core secondary structural elements in the DUF4136 domain that the original process did not contain.

Example 2

Improved Loop Modeling for PA3229

Figure 10:
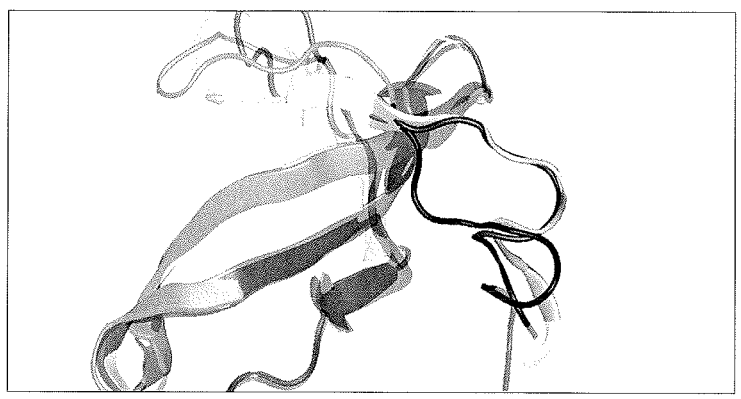
FIG. 10 depicts improvements achieved by the invention in predicting the structure of the PA3229 protein. The initial loop is highlighted to display the differences in the alignment of the improved model (light gray) to the known structure (dark gray) versus the original model (black).

The protein PA3229 from *Pseudomonas aeruginosa* PAO1 contains the domain DUF2790 [54] (PDB ID: 4F98). The loops that connect the core secondary structure features that define the domain can alter the entire structure. The protein model of PA3229 determined by the accelerated conformational sampling process predicted loops that more closely align with the experimentally determined structure than the model predicted using the original process (FIG. 10).

Example 3

Improved Alignment of the Mitochondrial Heat Shock Protein Prediction to the Experimentally Solved Structure The accelerated conformational sampling process created a model for the Mitochondrial heat shock protein which aligned to the known structure (PDB ID: 4PJ1) generally better than the model predicted using the original process.

Example 4

Improved Loop Modeling for Glo/EDI/BRP-Like Domain

Figure 11:
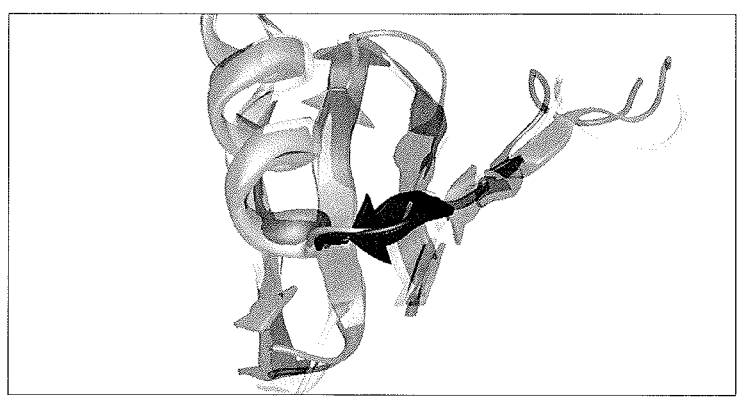
FIG. 11 depicts improvements achieved by the invention in predicting the structure of the Glo/EDI/BRP-like domain. Residues 12 to 61 are displayed for each structure with the loop in the forefront highlighted. The known experimental structure (dark gray) and improved model (light gray) designate this region as a loop, whereas the original model (black) designates it as a beta strand.

The glyoxalase/bleomycin resistance/dioxygenase protein from *Planctomyces limnophilus* dsm 3776 contains a Glo/EDI/BRP-like domain [55, 56] (PDB ID: 4RT5). The domain consists of alpha helices and beta strands connected by structured loops. The protein model predicted by the accelerated conformational sampling process correctly assigned the linking regions as loops—consistent with the experimentally determined structure—whereas the original process indicated additional secondary structure elements (FIG. 11).

Example 5

Improved Modeling for Med12BPR

The alignment of the experimentally determined structure of Med12BPR [57] (PDB ID: 4JQ6) and the models from both processes demonstrates that the accelerated conformational sampling process produced in a more accurate structure than the original process.

Example 6

Improved Secondary Structure for PP1826

Figure 12:
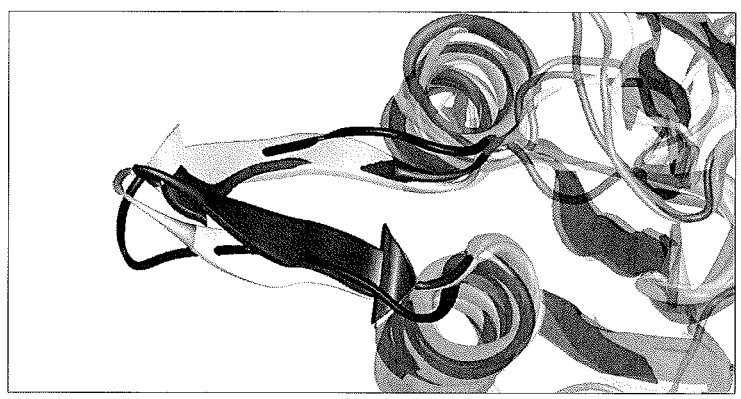
FIG. 12 depicts improvements achieved by the invention in predicting the structure of the PP1826 protein. The loop from residue 161 to 170 is highlighted to demonstrate the region in which both the experimental structure (dark gray) and improved model (light gray) classify the region to contain two beta strands, whereas the original model (black) contains a disordered loop.

The isochorismatase, PP1826, from *Pseudomonas putida* KT2440 contains the defined structural elements excepted for an isochorismastase [58] (PDB ID: 4H17). However, PP1826 has an additional linker composed of two beta strands which was discovered in the experimentally solved structure. The protein model created by the accelerated conformational sampling process correctly models this region as two beta strands as well as correctly modeling the core domain (FIG. 12). This is an improvement over the original process that modeled this region as an unordered loop.

Example 7

Improved Secondary Structure Assignment for LMOf2365-1307

Figure 13:
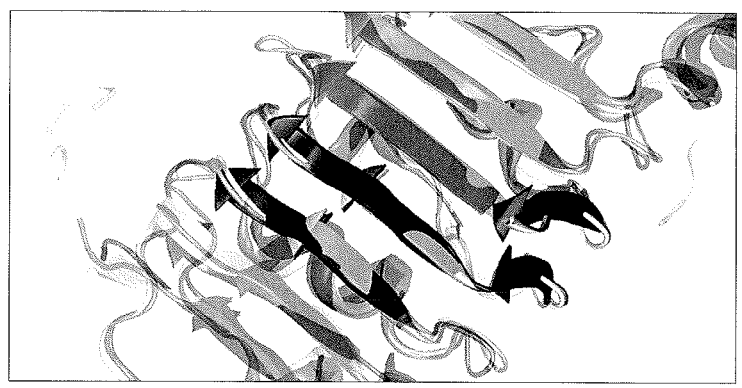
FIG. 13 depicts improvements achieved by the invention in predicting the structure of the LMOf2365-1307 protein. Highlighted are the regions in which the original model (black) incorrectly determined the secondary structure. There are two regions where the experimentally solved structure (dark gray) and the improved model (light gray) have loops where a beta strand was designated in the original model. Additionally two beta strands in the original model are each two residues longer than expected.

The structure of LMOf2365-1307 from *Listeria monocytogenes* strain 4b F2365 contains a large beta sheet comprised of seven parallel stands connected by alpha helices [59] (PDB ID: 4EZG). The protein model produced by the accelerated conformational sampling process contains beta stands that more closely match the length seen in the experimentally determined structure; whereas, the protein model determined by the original process inserted and extended additional beta strands (FIG. 13).

Example 8

Predicting Conformational Change in Antibody Structure Due to Site-Directed Mutation Antibodies are naturally occurring and synthetically produced molecules with widespread utility in disease diagnosis, immunoassays, and as immunotherapy agents. The present invention's ability to accurately predict the 3D structures of wild type or synthetic antibodies—such as antibody-drug conjugates (ADCs), humanized antibodies, and bispecific antibodies—can greatly aid the discovery of new biotherapeutics and accelerate their delivery to the clinical setting. Modifying known antibody sequences to alter the conformation, modulate affinity, or improve specificity are all tasks improved by accurate predictions of structural rearrangements induced by genetic variation and site-directed mutations. This is demonstrated for a single-chain antibody fragment (GenBank: ACA49231.1 residues 3-247) consisting of an IgV heavy chain joined to an IgV light chain by a linker sequence (TGGGGSGGGGSAGGGS) (SEQ ID No.: 1) where the accelerated conformational sampling process comprising the present invention predicted a structural change caused by a single site directed mutation, S158P. Two sets of fifty structural predictions were generated, one for the wild type sequence and one for the S158P mutation. To remove identical structures from the analysis, all pairwise structural alignments within a set were performed using TM-align [60] and identical structures (identified by a RMSD value of 0) were excluded. With the remaining structures from both sets, a multiple structure alignment with 3DCOMB [61] was performed to define a common frame of reference across the structures A confidence interval approach is used identify individual residues whose average location is significantly different between the two sets of structures, which is indicative of a conformational change. For each residue in each set, the average Cα atom location is calculated and a one-sided 95% confidence interval radius ($r_{95\%}$) is calculated $$r_{95\%} = \bar{d} + \frac{T_{n,95\%} \cdot s}{\sqrt{n}}$$

where $\bar{d}$ is the average of Cα distances from the average center, n is the number of structures, s is the standard deviation of Cα distances, and $T_{n,95\%}$ is the one-sided 95% t-statistic for a sample size of n. To perform the paired test, a sphere with radius $r_{95\%}$ is centered at the average location of the residue from the wild type structure set and a similar sphere is established for the mutant structure set. A residue is said to have experienced a conformational change due to the mutation if these two paired spheres do not overlap.

Figure 14:
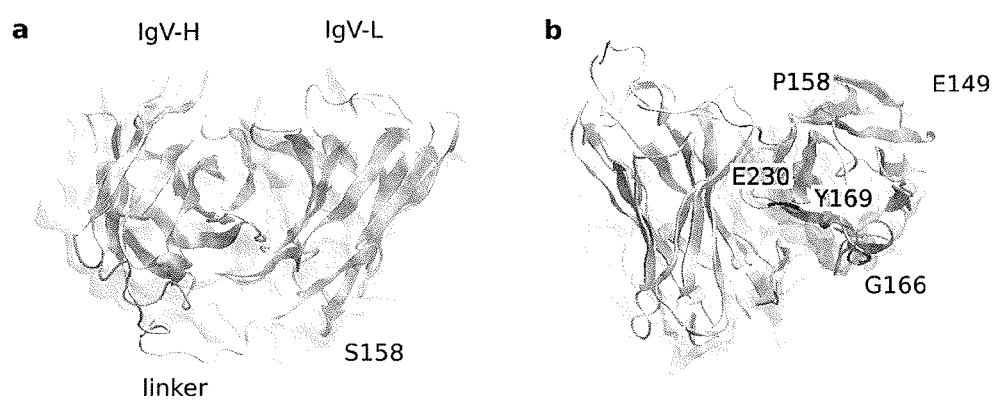
FIG. 14 illustrates the prediction of conformational changes induced by the S158P mutation in the single-chain antibody from Example 8, which consists of a variable heavy chain (IgV-H) and variable light chain (IgV-L) separated by a repeating linker. The location of the S158P mutation in the structure (a). Residues predicted to undergo a conformational change: E149, Y169, G166, and E230. These residues are sequentially and spatially separated from residue 158, illustrating that the NovaFold process can predict conformational changes at a distance (b).

For the example antibody, the mutation S158P is predicted to induce a conformational change for residues E149, Y169, G166, and E230 (FIG. 14). Notice that these predicted residues are separated from the mutation site in-sequence and spatially, illustrating that this approach applies to long-range regional changes rather than just the contacting residues around the site. The higher accuracy structures predicted by the accelerated conformational sampling process inherently improve the ability to predict conformational changes. This process will accelerate protein engineering efforts to design biotherapeutics, such as antibodies, to tune existing sequences to greater affinity or specificity for desired drug targets or to screen against mutations that deleteriously reconfigure existing binding sites.

Example 9

Accurate Prediction of Genetic Variation Causing Disease in Cancer Signaling Molecules The tumor suppressor protein p53 is inactivated by mutation in half of all human cancers [62]. The 393 residue protein has well-defined domains as well as natively unfolded regions that have a reversible equilibrium to form tetramers. Intrinsically, the wild type p53 protein is only marginally stable at body temperature. The N-terminal regions include a 62 residue transactivation domain, a 31 residue proline-rich region containing SH3-domain binding motifs, and a 198 residue central core domain that binds DNA. Experimental structures exist for the p53 core domain and oligomerization domains, but not for the full length protein. The p53 tumor suppressor is a relevant target in cancer biology with incomplete structural information. As such, researchers are limited in determining the structural mechanism of genetic variation associated with cancer caused by the deregulation of p53. Structure predictions produced by the accelerated conformational sampling process empower clinical researchers to discover the causal relationship between missense mutations observed in patients and the structural mechanism causing their disease.

Figure 15:
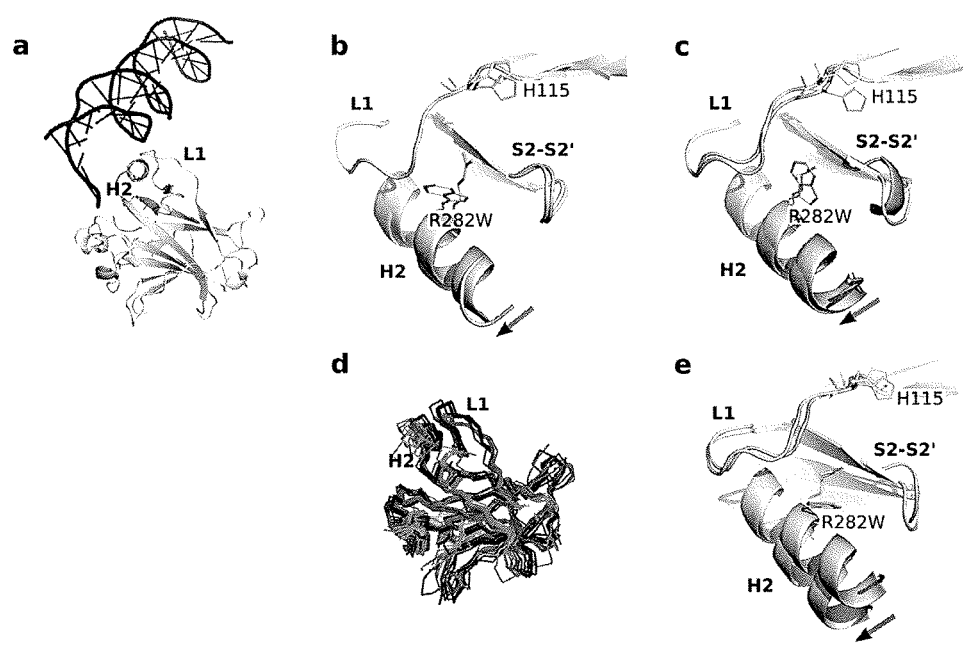
FIG. 15 illustrates the use of the synthetic template method to accurately predict the effect of genetic variation in the DNA-binding sites of the p53 oncoprotein. Major DNA binding surfaces of p53 are formed by loops L2, L3, and the loop-sheet-helix motif (loop L1, beta-strands S2 and S2', S10, and helix H2) (a). The superimposed crystallographic structures of the core domain of the p53 wild-type (PDB: 1TUP) and the R282W mutant (PDB: 2J21) (b). The mutation drives a separation of the H2 helix and destabilizes the L1 loop. When the structures of wild type and the R282W mutant are predicted by the NovaFold process without the synthetic template method, these features are matched but the movements of the H2 helix are improperly constrained (c). An ensemble of synthetic templates created by the NovaFold process for improved modeling of the p53 core domain (d). By applying the accelerated conformational sampling method, the increased structural dynamics successfully model the movement of the H2 helix to better accommodate the bulky W282 sidechain (e).

Many of the 1300 cancer-related missense mutations in p53 are observed in the core domain [62]. Some mutations increase stability, such as N239Y and N268D, by rigidifying the protein's structure, but most decrease structural stability and induce structural changes, including V143A, Y220C, C242S, and R282W. The NovaFold process comprising the accelerated conformational sampling process was used to model the wild type p53 DNA-binding core (UniProt: P04637, residues 96-290) and the R282W mutation. The wild type and mutant structures were predicted by the original process and, subsequently, the accelerated conformational sampling method using ten synthetic templates perturbed along pairwise combinations of the ten lowest-frequency normal modes of motion. The structure predictions were aligned to the experimental wild type (PDB: 1TUP) and mutant (PDB: 2J21) structures. As a control, these two structures were excluded from the selected templates for the modeling process. The structure predictions are compared in FIG. 15. The original process predicts a minor movement of the H2 and L1 helix for the R282W mutation; however, the accelerated conformational sampling process further deforms the region into the correct, near-native conformation. In this case, the increased structural diversity of the invention process resulted in an improved ability to rapidly survey dynamic protein conformation changes. Experimental structure determination is time and cost prohibitive for screening thousands of variants; however, NovaFold (including the synthetic template process) only requires a commodity computer workstation and one to three days of computer time to predict whether a mutation destabilizes a protein fold from a conformational change. Thus, the invention can be used to classify observed missense mutations in patients by their predicted mode of structural destabilization. This information will aid clinicians in selecting the most effect treatment for a given mutation.

Example 10

Improving Diversity of Templates in Prediction of Membrane Protein Structures.

Figure 16:
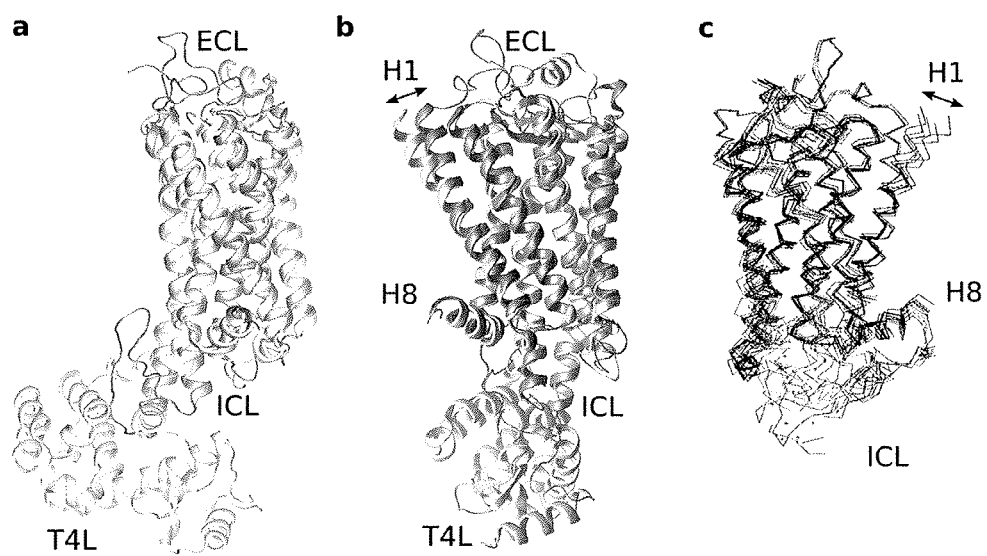
FIG. 16 illustrates how synthetic templates can aid the prediction of membrane protein families including the G Protein-Coupled Receptors (GPCRs). Experimentally solving GPCR structures remains a difficult challenge; as such, the human Beta-2 adrenergic receptor (B2AR) required protein engineering efforts to replace large intracellular loops to solve the structure [41]. The B2AR structure (PDB: 2RH1, blue) fused with T4-ligase (T4L, orange) is shown (a-b). The NovaFold process can greatly accelerate the study of GPCR proteins, which predicted the structure of the unsolved murine B2AR protein (tan). The predicted structure using the original algorithm is aligned against human B2AR for comparison (a-b). When comparing the known human and the original predicted murine structures, the N-terminal transmembrane helix H1 deviates in the predicted model when the intracellular loops are modeled instead of T4L (b). The use of synthetic templates in the present invention improves the structural diversity of GPCR modeling and accelerates the sampling of conformations more similar to the experimental H1 helix conformation observed in the human B2AR structure (c).

G Protein-Coupled Receptors (GPCR) are the largest class of membrane proteins in the human genome with almost 1000 members in human genome [41]. As such, drugs that target GPCRs constitute 50% current market of human therapeutics. The determination of GPCR structures remains a challenging endeavor and there are fewer than 30 solved GPCR proteins available in the PDB. Filling in this large gap of unsolved GPCR structures will be a combined experimental and computational challenge. NovaFold produced a novel model for the murine Beta-2 adrenergic receptor (B2AR) based on the existing structural information present in the PDB; however, due to the limited quantity of solved GPCR structures, the original process only identifies 15 unique templates. The new process addresses the lack of diversity of templates and produced an additional 10 unique templates with improved diversity that captured the flexibility of the intracellular and extracellular loop regions of GPCRs and transmembrane helices. The positioning of the Helix I (30-60), Helix II (67-96), Helix V (197-229), and the orientations of the intracellular loops (ICL) are altered in the diverse pool of synthetic templates to provide an accelerated sampling of the conformational space of these flexible regions for structure prediction (FIG. 16).

Example 11

Determining Molecular Binding Specificity in the Context of Structural Flexibility.

The NovaFold process may be used to determine binding site specificity for enzyme substrates, allosteric effectors, and receptor-ligand complexes as well as more general protein-protein and protein-small molecule interactions. Accelerated conformational sampling can determine the limits of conformational plasticity that a given protein sequence can assume over the course of accommodating a substrate or effector molecule, resulting in a discrete range of possible binding site sizes and geometries. As such, the NovaFold process is especially useful for evaluating competitive or non-competitive inhibitors' ability to block substrates or allosteric effectors from binding. The process for using accelerated conformational sampling on the binding site of an enzyme-substrate or enzyme-effector complex is similar to that described in the preceding Examples, but with two key differences. First, normal mode sampling is shifted from low frequency modes associated with large concerted movements to higher frequency modes associated with localized fluctuations, typically between modes 20 through 50. Second, conformational sampling is restricted such that intermolecular contacts with the ligand or intramolecular contacts within the site are preserved. This is enforced by constructing distance restraints embodying the contacts and evaluating them as part of the "Test Chemical Linkages" step in FIG. 8. In certain instances knowledge of an enzyme mechanism can be exploited as constraints to limit the conformational possibilities defined in the NovaFold process. As an example, the structure of a typical serine protease in complex with its substrate is constrained by the mechanistic requirement that the Asp-His-Ser catalytic triad be in an approximately linear arrangement relative to the alpha-amino group of the cleavage substrate, which facilitates formation of the enzyme-substrate intermediate. In this case, both distance and angular restraints representing the hydrogen bonds between the acid, base, and nucleophile are enforced during the process. This arrangement is not guaranteed to represent the global minimum energy conformation for either the enzyme or the substrate; however, as demanded by the chemical mechanism, it is necessary to constrain the catalytic triad in order to accurately model the protease-substrate complex. Combined with these restraints, the NovaFold process explores the accessible conformational space by systematically rejecting mechanistically unfavorable alternatives to produce the best model of such a complex. A similar approach can be used to model alternate conformations associated with allosteric interactions.

REFERENCES

1. Anfinsen C B. Principles that govern the folding of protein chains. Science. 1973; 181(4096):223-30.
2. Sadowski M I, Jones D T. The sequence-structure relationship and protein function prediction. Current opinion in structural biology. 2009; 19(3):357-62.
3. Berman H M, Westbrook J D, Gabanyi M J, Tao W, Shah R, Kouranov A, et al. The protein structure initiative structural genomics knowledgebase. Nucleic acids research. 2009; 37(Database issue):D365-8.
4. Committee. Protein Structure Initiative Update. Bethesda, Md.: National Institute of General Medical Sciences (NIH), 2007 May 2007. Report No.
5. Schmitz C, Vernon R, Otting G, Baker D, Huber T. Protein structure determination from pseudocontact shifts using ROSETTA. Journal of molecular biology. 2012; 416(5): 668-77.
6. Rodrigues J P, Levitt M, Chopra G. KoBaMIN: a knowledge-based minimization web server for protein structure refinement. Nucleic acids research. 2012:40(Web Server issue):W323-8.
7. Liwo A, Lee J, Ripoll D R, Pillardy J, Scheraga H A. Protein structure prediction by global optimization of a potential energy function. Proceedings of the National Academy of Sciences of the United States of America. 1999; 96(10):5482-5.
8. Zhou H, Skolnick J. Template-based protein structure modeling using TASSER(VMT). Proteins. 2011.
9. Zhang Y. Protein structure prediction: when is it useful? Current opinion in structural biology. 2009; 19(2):145-55.
10. Park H, Hwang K Y, Oh K H, Kim Y H, Lee J Y, Kim K. Discovery of novel alpha-glucosidase inhibitors based on the virtual screening with the homology-modeled protein structure. Bioorganic & medicinal chemistry. 2008; 16(1):284-92.
11. Park H, Bahn Y J, Jung S K, Jeong D G, Lee S H, Seo I, et al. Discovery of novel Cdc25 phosphatase inhibitors with micromolar activity based on the structure-based virtual screening. Journal of medicinal chemistry. 2008; 51(18):5533-41.
12. Hellmuth K, Grosskopf S, Lum C T, Wurtele M, Roder N, von Kries J P, et al. Specific inhibitors of the protein tyrosine phosphatase Shp2 identified by high-throughput docking. Proceedings of the National Academy of Sciences of the United States of America. 2008; 105(20): 7275-80.
13. Cozza G, Gianoncelli A, Montopoli M, Caparrotta L, Venerando A, Meggio F, et al. Identification of novel protein kinase CK1 delta (CK1delta) inhibitors through structure-based virtual screening. Bioorganic & medicinal chemistry letters. 2008; 18(20):5672-5.
14. Strambi A, Mori M, Rossi M, Colecchia D, Manetti F, Carlomagno F, et al. Structure prediction and validation of the ERK8 kinase domain. PloS one. 2013; 8(1):e52011. Epub 2013/01/18. doi: 10.1371/journal.pone.0052011.
15. Xiang Z, Soto C S, Honig B. Evaluating conformational free energies: the colony energy and its application to the problem of loop prediction. Proceedings of the National Academy of Sciences of the United States of America. 2002; 99(11):7432-7.
16. Eswar N, Eramian D, Webb B, Shen M Y, Sali A. Protein structure modeling with MODELLER. Methods in molecular biology. 2008; 426:145-59.
17. Wallner B, Larsson P, Elofsson A. Pcons.net: protein structure prediction meta server. Nucleic acids research. 2007; 35(Web Server issue):W369-74.
18. Bordoli L, Kiefer F, Arnold K, Benkert P, Battey J, Schwede T. Protein structure homology modeling using SWISS-MODEL workspace. Nature protocols. 2009; 4(1):1-13.
19. Bowie J U, Luthy R, Eisenberg D. A method to identify protein sequences that fold into a known three-dimensional structure. Science. 1991; 253(5016):164-70.
20. Vallat B K, Pillardy J, Majek P, Meller J, Blom T, Cao B, et al. Building and assessing atomic models of proteins from structural templates: learning and benchmarks. Proteins. 2009; 76(4):930-45.
21. Sasson I, Fischer D. Modeling three-dimensional protein structures for CASP5 using the 3D-SHOTGUN meta-predictors. Proteins. 2003; 53 Suppl 6:389-94.
22. Jones D T, Bryson K, Coleman A, McGuffin L J, Sadowski M I, Sodhi J S, et al. Prediction of novel and analogous folds using fragment assembly and fold recognition. Proteins. 2005; 61 Suppl 7:143-51.
23. Xu J, Li M, Kim D, Xu Y. RAPTOR: optimal protein threading by linear programming. Journal of bioinformatics and computational biology. 2003; 1(1):95-117.
24. Soding J. Protein homology detection by HMM-HMM comparison. Bioinformatics. 2005; 21(7):951-60.
25. Bennett-Lovsey R M, Herbert A D, Sternberg M J, Kelley L A. Exploring the extremes of sequence/structure space with ensemble fold recognition in the program Phyre. Proteins. 2008; 70(3):611-25.
26. Cao R, Bhattacharys D, Li J, Adhikari B, Cheng J, editors. Tertiary structure prediction by the MULTICOM human group. CASP 11; 2014 Dec. 7-10; Riviera Maya, Mexico.
27. Joo K, al. e, editors. Protein structure modeling by global optimization. CASP 11; 2014 Dec. 7-10; Riviera Maya, Mexico.
28. Kim D E, Ovchinnikov S, Wang R, DiMaio F, Baker D, editors. Robetta: Full-chain protein structure prediction server for CASP11. CASP 11; 2014 Dec. 7-10; Riviera Maya, Mexico.

29. Mabrouk M, Putz I, Werner T, Schneider M, Brock O, editors. Leveraging novel information sources for protein structure prediction. CASP 11; 2014 Dec. 7-10; Riviera Maya, Mexico.
30. Zhang Y, Yang J, Zhang W, editors. Protein structure predictions by Zhang human group in CASP11. CASP 11; 2014 Dec. 7-10; Riviera Maya, Mexico.
31. Ghouzam Y, Gelly J C, editors. Protein structure prediction based on fold recognition using profile-profile and structural alphabet. CASP 11; 2014 Dec. 7-10; Riviera Maya, Mexico.
32. Le Q, Pollastri G, Koehl P, editors. Structural alphabets for protein structure classification: A comparative study. CASP 11; 2014 Dec. 7-10; Riviera Maya, Mexico.
33. Zhang Y. I-TASSER: fully automated protein structure prediction in CASP8. Proteins. 2009; 77 Suppl 9:100-13.
34. Zhang Y. Template-based modeling and free modeling by I-TASSER in CASP7. Proteins. 2007; 69 Suppl 8:108-17.
35. Wu S, Skolnick J, Zhang Y. Ab initio modeling of small proteins by iterative TASSER simulations. BMC biology. 2007; 5:17.
36. Roy A, Kucukural A, Zhang Y. I-TASSER: a unified platform for automated protein structure and function prediction. Nature protocols. 2010; 5(4):725-38.
37. Zhang Y. I-TASSER server for protein 3D structure prediction. BMC bioinformatics. 2008; 9:40.
38. Xu D, Zhang J, Roy A, Zhang Y. Automated protein structure modeling in CASP9 by I-TASSER pipeline combined with QUARK-based ab initio folding and FG-MD-based structure refinement. Proteins. 2011; 79 Suppl 10:147-60.
39. Roy A, Xu D, Poisson J, Zhang Y. A protocol for computer-based protein structure and function prediction. J Vis Exp. 2011: (57):e3259.
40. Moult J. A decade of CASP: progress, bottlenecks and prognosis in protein structure prediction. Current opinion in structural biology. 2005; 15(3):285-9.
41. Cherezov V, Rosenbaum D M, Hanson M A, Rasmussen S G, Thian F S, Kobilka T S, et al. High-resolution crystal structure of an engineered human β2-adrenergic G protein-coupled receptor. Science. 2007; 318(5854):1258-65.
42. Altschul S F, Madden T L, Schaffer A A, Zhang J, Zhang Z, Miller W, et al. Gapped BLAST and PSI-BLAST: a new generation of protein database search programs. Nucleic acids research. 1997; 25(17):3389-402.
43. Doruker P, Atilgan A R, Bahar I. Dynamics of proteins predicted by molecular dynamics simulations and analytical approaches: application to alpha-amylase inhibitor. Proteins. 2000; 40(3):512-24.
44. Atilgan A R, Durell S R, Jernigan R L, Demirel M C, Keskin O, Bahar I. Anisotropy of fluctuation dynamics of proteins with an elastic network model. Biophys J. 2001; 80(1):505-15.
45. Zhang Y, Kolinski A, Skolnick J. TOUCHSTONE II: a new approach to ab initio protein structure prediction. Biophys J. 2003; 85(2):1145-64. doi: 10.1016/S0006-3495(03)74551-2.
46. Karplus M, Petsko G A. Molecular dynamics simulations in biology. Nature. 1990; 347(6294):631-9.
47. Karplus M, McCammon J A. Molecular dynamics simulations of biomolecules. Nat Struct Biol. 2002; 9(9):646-52.
48. Wells S, Menor S, Hespenheide B, Thorpe M F. Constrained geometric simulation of diffusive motion in proteins. Phys Biol. 2005; 2(4):S127-36.
49. Wilson E B, Decius J C, Cross P C. Molecular vibrations: the theory of infrared and Raman vibrational spectra: Courier Corporation; 2012.
50. LaValle S M. Rapidly-Exploring Random Trees A Цew Tool for Path Planning. 1998.
51. Liu F, Harada T, Lee Y, Kim Y J, editors. Real-time collision culling of a million bodies on graphics processing units. ACM Transactions on Graphics (TOG); 2010: ACM.
52. Shellshear E. 1D sweep-and-prune self-collision detection for deforming cables. The Visual Computer. 2014; 30(5):553-64.
53. Xu J, Bjursell M K, Himrod J, Deng S, Carmichael L K, Chiang H C, et al. A genomic view of the human-*Bacteroides* thetaiotaomicron symbiosis. Science. 2003; 299(5615):2074-6.
54. Stover C K, Pham X Q, Erwin A L, Mizoguchi S D, Warrener P, Hickey M J, et al. Complete genome sequence of *Pseudomonas aeruginosa* PAO1, an opportunistic pathogen. Nature. 2000; 406(6799):959-64.
55. Labutti K, Sikorski J, Schneider S, Nolan M, Lucas S, Glavina Del Rio T, et al. Complete genome sequence of *Planctomyces limnophilus* type strain (Mu 290). Stand Genomic Sci. 2010; 3(1):47-56.
56. Marchler-Bauer A, Derbyshire M K, Gonzales N R, Lu S, Chitsaz F, Geer L Y, et al. CDD: NCBI's conserved domain database. Nucleic acids research. 2015; 43(Database issue):D222-6.
57. Ran T, Ozorowski G, Gao Y, Sineshchekov O A, Wang W, Spudich J L, et al. Cross-protomer interaction with the photoactive site in oligomeric proteorhodopsin complexes. Acta Crystallogr D Biol Crystallogr. 2013; 69(Pt 10):1965-80.
58. Caruthers J, Zucker F, Worthey E, Myler P J, Buckner F, Van Voorhuis W, et al. Crystal structures and proposed structural/functional classification of three protozoan proteins from the isochorismatase superfamily. Protein Sci. 2005; 14(11):2887-94.
59. Camejo A, Buchrieser C, Couve E, Carvalho F, Reis O, Ferreira P, et al. In vivo transcriptional profiling of *Listeria monocytogenes* and mutagenesis identify new virulence factors involved in infection. PLoS Pathog. 2009; 5(5):e1000449.
60. Zhang Y, Skolnick J. T M-align: a protein structure alignment algorithm based on the TM-score. Nucleic acids research. 2005; 33(7):2302-9.
61. Wang S, Peng J, Xu J. Alignment of distantly related protein structures: algorithm, bound and implications to homology modeling. Bioinformatics. 2011; 27(18):2537-45.
62. Joerger A C, Fersht A R. Structure-function-rescue: the diverse nature of common p53 cancer mutants. Oncogene. 2007; 26(15):2226-42.

What is claimed is:

1. A conformational sampling method for predicting the structure of an amino acid sequence, the amino acid sequence comprising a plurality of residues, comprising: a) creating a sequence profile matrix of the amino acid sequence; b) determining an alignment of each respective residue of the amino acid sequence against the sequence profile matrix; c) identifying internal residue contacts for one or more residues in the plurality of residues using the alignment; d) collecting the features of the sequence profile matrix and internal residue contacts for each residue in the plurality of residues into a collected feature matrix; e) aligning the collected feature matrix using one or more threading models with a structural feature database of original templates; f) selecting a plurality of optimally aligned original templates from the aligning e); g) calculating normal modes of motion for each original template in the plurality of optimally aligned original templates; h) perturbing each respective original template in the plurality of optimally aligned original templates, for each pair of calculated normal modes, thereby collectively creating a plurality of synthetic templates; i) scoring the energy difference between each original template and the corresponding synthetic template; j) selecting a subset of synthetic templates from the plurality of synthetic templates based on satisfaction of a predetermined cut-off criterion; k) replacing or supplementing the original templates in the plurality of optimally aligned original templates with the corresponding selected subset of synthetic templates to generate a plurality of modeling templates; l) calculating distance and contact restraints within modeling templates of the plurality of modeling templates; m) performing, with modeling templates in the plurality of modeling templates, Markov Chain Monte Carlo simulations, thereby obtaining simulation results; n) clustering the simulation results, wherein the clustering comprises a plurality of clusters, each cluster in the plurality of clusters representing models from the performing m); o) selecting representative models of each cluster in the plurality of clusters; p) refining the representative models of the selecting o) by energy minimization; and q) selecting the lowest energy refined representative model as the predicted structure of the amino acid sequence.

2. The method of claim 1, wherein creating the sequence profile matrix comprises predicting the secondary structure of the amino acid sequence.

3. The method of claim 1, wherein creating the sequence profile matrix comprises predicting solvent accessibility of the amino acid sequence.

4. The method of claim 1, wherein the predetermined cut-off criterion is a predetermined percentile score and the predetermined percentile score is the 65th percentile.

5. The method of claim 1, wherein the original templates of k) are supplemented with the corresponding subset of selected synthetic templates.

6. The method of claim 1, wherein the original templates of k) are replaced with the corresponding subset of selected synthetic templates.

7. A computer system for predicting the structure of an amino acid sequence, the amino acid sequence comprising a plurality of residues, the computer system comprising at least one processor and memory storing at least one program for execution by the at least one processor, the at least one program comprising instructions for: a) creating a sequence profile matrix of the amino acid sequence; b) determining an alignment of each respective residue of the amino acid sequence against the sequence profile matrix; c) identifying internal residue contacts for one or more residues in the plurality of residues using the alignment; d) collecting the features of the sequence profile matrix and internal residue contacts for each residue in the plurality of residues into a collected feature matrix; e) aligning the collected feature matrix using one or more threading models with a structural feature database of original templates; f) selecting a plurality of optimally aligned original templates from the aligning e); g) calculating normal modes of motion for each original template in the plurality of optimally aligned original templates; h) perturbing each respective original template in the plurality of optimally aligned original templates, for each pair of calculated normal modes, thereby collectively creating a plurality of synthetic templates; i) scoring the energy difference between each original template and the corresponding synthetic template; j) selecting a subset of synthetic templates from the plurality of synthetic templates based on satisfaction of a predetermined cut-off criterion; k) replacing or supplementing the original templates in the plurality of optimally aligned original templates with the corresponding selected subset of synthetic templates to generate a plurality of modeling templates; l) calculating distance and contact restraints within modeling templates of the plurality of modeling templates; m) performing, with modeling templates in the plurality of modeling templates, Markov Chain Monte Carlo simulations, thereby obtaining simulation results; n) clustering the simulation results, wherein the clustering comprises a plurality of clusters, each cluster in the plurality of clusters representing models from the performing m); o) selecting representative models of each cluster in the plurality of clusters; p) refining the representative models of the selecting o) by energy minimization; and q) selecting the lowest energy refined representative model as the predicted structure of the amino acid sequence.

8. The computer system of claim 7, wherein creating the sequence profile matrix comprises predicting the secondary structure of the amino acid sequence.

9. The computer system of claim 7, wherein creating the sequence profile matrix comprises predicting solvent accessibility of the amino acid sequence.

10. The computer system of claim 7, wherein the predetermined cut-off criterion is a predetermined percentile score and the predetermined percentile score is the 65th percentile.

11. The computer system of claim 7, wherein the original templates of k) are supplemented with the corresponding subset of selected synthetic templates.

12. The computer system of claim 7, wherein the original templates of k) are replaced with the corresponding subset of selected synthetic templates.

13. A non-transitory computer readable storage medium storing a computational module for predicting the structure of an amino acid sequence, the amino acid sequence comprising a plurality of residues, the computational module comprising instructions for: a) creating a sequence profile matrix of the amino acid sequence; b) determining an alignment of each respective residue of the amino acid sequence against the sequence profile matrix; c) identifying internal residue contacts for one or more residues in the plurality of residues using the alignment; d) collecting the features of the sequence profile matrix and internal residue contacts for each residue in the plurality of residues into a collected feature matrix; e) aligning the collected feature matrix using one or more threading models with a structural feature database of original templates; f) selecting a plurality of optimally aligned original templates from the aligning e); g) calculating normal modes of motion for each original template in the plurality of optimally aligned original templates; h) perturbing each respective original template in the plurality of optimally aligned original templates, for each pair of calculated normal modes, thereby collectively creating a plurality of synthetic templates; i) scoring the energy difference between each original template and the corresponding synthetic template; j) selecting a subset of synthetic templates from the plurality of synthetic templates based on satisfaction of a predetermined cut-off criterion; k) replacing or supplementing the original templates in the plurality of optimally aligned original templates with the corresponding selected subset of synthetic templates to generate a plurality of modeling templates; l) calculating distance and contact restraints within modeling templates of the plurality of modeling templates; m) performing, with modeling templates in the plurality of modeling templates, Markov Chain Monte Carlo simulations, thereby obtaining simulation results; n) clustering the simulation results, wherein the clustering comprises a plurality of clusters, each cluster in the plurality of clusters representing models from the performing m); o) selecting representative models of each cluster in the plurality of clusters; p) refining the representative models of the selecting o) by energy minimization; and q) selecting the lowest energy refined representative model as the predicted structure of the amino acid sequence.

14. The non-transitory computer readable storage medium of claim 13, wherein creating the sequence profile matrix comprises predicting the secondary structure of the amino acid sequence.

15. The non-transitory computer readable storage medium of claim 13, wherein creating the sequence profile matrix comprises predicting solvent accessibility of the amino acid sequence.

16. The non-transitory computer readable storage medium of claim 13, wherein the predetermined cut-off criterion is a predetermined percentile score and the predetermined percentile score is the 65th percentile.

17. The non-transitory computer readable storage medium of claim 13, wherein the original templates of k) are supplemented with the corresponding subset of selected synthetic templates.

18. The non-transitory computer readable storage medium of claim 13, wherein the original templates of k) are replaced with the corresponding subset of selected synthetic templates.

* * * * *

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
```

```
<220> FEATURE:
<223> OTHER INFORMATION: linker sequence

<400> SEQUENCE: 1

Thr Gly Gly Gly Gly Ser Gly Gly Gly Ser Ala Gly Gly Gly Ser
1               5                   10                  15
```